(12) United States Patent
Berry

(10) Patent No.: US 6,423,000 B1
(45) Date of Patent: Jul. 23, 2002

(54) LABOR MONITORING DEVICE

(76) Inventor: Daniel K. Berry, 135 Vinsant St., Brooks AFB, TX (US) 78235-1015

( * ) Notice: Subject to any disclaimer, the term of this patent is extended or adjusted under 35 U.S.C. 154(b) by 10 days.

(21) Appl. No.: 09/702,617

(22) Filed: Nov. 1, 2000

(51) Int. Cl.$^7$ .............................. A61B 5/00; A61B 5/103; A61B 5/117
(52) U.S. Cl. .................... 600/304; 600/591; 600/588
(58) Field of Search ................................ 600/304, 591, 600/588, 587, 376

(56) References Cited

U.S. PATENT DOCUMENTS

| | | | | |
|---|---|---|---|---|
| 4,141,345 A | * | 2/1979 | Allen et al. ................. | 600/591 |
| 4,432,376 A | * | 2/1984 | Huszar ....................... | 600/587 |
| 4,966,152 A | * | 10/1990 | Gang et al. ................. | 600/453 |
| 5,807,281 A | * | 9/1998 | Welch ......................... | 600/588 |
| 5,876,357 A | * | 3/1999 | Tomer ........................ | 600/591 |
| 6,039,701 A | * | 3/2000 | Silwa et al. ................ | 600/588 |

* cited by examiner

Primary Examiner—Kevin Shaver
Assistant Examiner—Navin Natnithithadha
(74) Attorney, Agent, or Firm—Peter A. Borsari

(57) ABSTRACT

A device for implantation on the cervix of a pregnant female that provides monitoring means by which the dilatation of a female patient's cervix may be monitored during the first phase of labor. The device comprises a housing manufactured from biocompatible material into which a spindle member joined to a tension sensor passes. The housing also contains a transmitter and a power source for the sensor and transmitter. A plurality of sutures are fixed the spindle and pass out of housing so that they may be attached to the female patient's cervix. A tension knob is provided for winding excess suture length onto the spindle, thereby securing the device within the vagina. Dilatation of the cervix at the onset of labor exerts tension on the sutures which is conveyed to the spindle and translated by the sensor to a signal directed at the transmitter. Throughout the first phase of labor, the transmitter issues electronic signals to a second electronic device such as a computer, allowing the compilation and display of dilatation data.

8 Claims, 4 Drawing Sheets

LABOR MONITORING DEVICE

FIELD OF INVENTION

The present invention relates to the monitoring of the state of cervical dilatation in a pregnant female mammal who is in the first phase of labor. More particularly, the present invention relates to a sensor device which may be implanted in the female's cervix which is capable of sensing the amount of dilatation of the cervix during the first phase of labor and of transmitting a signal to an auxiliary electronic device such as a computer. Continuous monitoring of the state of dilatation by the sensor thus may be translated into a graphical representation easily viewable by an attending health caregiver.

BACKGROUND OF THE INVENTION

It is often difficult for a pregnant woman to know when labor has begun. For example, during the last trimester of pregnancy, false labor comprising irregular and shallow contractions of the uterus, the so-called "Braxton Hicks contractions", may be confused with actual labor. Unlike true labor, these contractions are highly irregular and may be felt in the abdomen at onset rather than in the back. Furthermore, Braxton Hicks contractions are weak and do not strengthen. Despite these distinguishing characteristics, many women, especially those lacking competent care, may not be able to tell the difference between false labor and actual labor.

During the latent phase of labor (pre labor) the cervix begins thinning out and may dilate very gradually. The first stage of labor is generally considered to begin when the cervix starts to open and ends when it is filly open. Women are admitted to the hospital when the dilation of the cervix reaches about 4 cm. The vagina may be examined to determine if the membranes surrounding the fetus have ruptured and to measure how dilated and effaced the cervix is. To save the woman's energy and to avoid tearing her cervix, pushing is discouraged during the first stage of labor which may last anywhere from a few hours to 12 hours. Pushing efforts are needed during the second stage of labor which begins when the cervix has achieved a maximum dilation of about 10 cm.

In some instances, rupture of the fluid-filled membranes surrounding the fetus may occur before labor begins (the water breaks), causing leakage of the amniotic fluid through the cervix and vagina and requiring immediate medical attention. In most of these cases, labor spontaneously begins within 24 hours from the time the water breaks. In cases where labor fails to begin, labor is induced to prevent infections caused by bacteria entering the uterus from the vagina. Because the release of the amniotic fluid does not always occur as a sudden gush and may be a slow trickle resembling urinary leakage, a woman may not always be sure that her water has broken and she may fail to seek medical attention promptly. This delay may cause stress to the fetus and may endanger the health of mother and child.

"Silent labor" is a situation in which labor onset occurs without pronounced contractions. This condition occurs commonly in premature birth situations where dilatation and effacement of the cervix are not accompanied with contractions. In some cases, contractions may not begin until minutes before actual delivery.

Determining the onset of labor in non-human females may be even more unpredictable due to the inability of the animal to discuss its condition with its human caregivers. As with human labor, complications are possible which endanger both mother and children.

Once dilatation has begun, it may not proceed in a linear fashion, requiring medical personnel to repeatedly measure the amount of dilation which has occurred. In standard procedures, this involves the insertion of fingers or instruments into a woman's vagina to take measurements, taxing the time of busy personnel and the patience of the patient who is in an already uncomfortable state.

Numerous attempts have been made to provide means by which onset and conditions of labor may be evaluated and/or monitored. For example, U.S. Pat. No. 5,807,281 to Welch shows an apparatus for detecting dilation of a cervix by measuring the force exerted by a cervix as it dilates at the onset of labor. The device comprises a ring-shaped element in series with an enclosure that encircles the cervix and is secured thereto by a friction tab. The enclosure contains a detectable fluid or particulate material which is released by the device to signal that the dilation has occurred.

U.S. Pat. No. 5,406,961 to Artal relates to a premature labor monitor system including a pessary having sensing means for determining the dilation and effacement of the cervix of a patient. Sensing means are provided which determine changes in the energy levels transmitted through the cervical tissue as the tissue thins and loses vascularization during the labor process. Signals are transmitted from the pessary to a patient monitor by such means as small data wires or microwave transmission generated by a small transmitter on the pessary.

U.S. Pat. No. 3,768,459 to Cannon et al. discloses a cervical dilation measuring device comprising a signal transmitting device that may be attached to one side of the cervix and a miniature receiving device attached to or placed against the opposite side of the cervix. The intensity of the signal passed from the transmitting device to the receiving device will vary as a function of the distance of separation of the devices indicating the current dilation of the cervix. Similarly, U.S. Pat. No. 5,438,996 to Kemper et al.; U.S. Pat. No. 5,851,188 to Bullard et al. and U.S. Pat. No. 5,713,371 to Sherman et al. disclose devices having transducers which are positioned on the cervix and which utilize ultrasound to determine the dilation of the cervix.

U.S. Pat. No. 4,476,871 to Hon teaches a device for monitoring cervical dilatation during labor comprising an elongated member adapted for positioning between a fetal presenting part and the cervix. Means are provided for measuring the recession of the cervix with cervical dilatation from the elongated member and along the longitudinal axis thereof.

U.S. Pat. No. 5,876,357 to Tomer relates to a labor monitoring system using a probe in the form of a linear caliper-clamp apparatus and a flexible membrane which are manually inserted into the vagina and clamped on the cervix wall. The arms of the caliper straddle the thickness of the cervical wall and the flexible membrane approximates the radius of curvature of the opening of the cervix. Sensors are used to relate this data to a monitoring unit and data processing apparatus such as a computer.

U.S. Pat. Nos. 4,719,925 and 4,682,609 both to Parsons and U.S. Pat. No. 4,207,902 Krementsov each relate to hand-actuated measuring apparatuses having a scissors-like action which may be inserted into the vagina to determine the dilatation of the cervix.

U.S. Pat. No. 3,583,389 to Harvey; U.S. Pat. No. 4,203,450 to Kegel; U.S. Pat. No. 4,055,839 to Skeggs; U.S. Pat. No. 4,264,900 to Charlier; U.S. Pat. No. 4,232,686 to Kammlade, Jr.; U.S. Pat. No. 5,776,073 to Garfield et al.; U.S. Pat. No. 5,450,837 to Garfield et al.; U.S. Pat. No.

5,879,293 to Hojaiban et al. each teach apparatuses which monitor cervical and/or other labor conditions but which are non-invasive, deriving their output from sensors applied on or about the body surface of a female patient.

What is needed are means to monitor conditions of labor that may be secured rapidly and easily to the female body and to provide to medical caregivers data regarding conditions relevant to a pregnant female subject's cervix. The desired means should not be obtrusively large or unduly delicate in use such that they do not pose a burden to the female patient/subject or suffer damage under normal conditions of use. The means, moreover, should continuously apprise a patient or her health caregiver of the state of dilatation of her cervix.

SUMMARY OF THE INVENTION

Accordingly, it is an objective of the present invention to provide a device which can sense a condition of the cervix of a pregnant female and to convey information regarding the sensed condition to a health caregiver or to the patient herself at the onset of labor.

It is a further objective of the invention to provide a device which is manufactured from bio-compatible materials and may be passed safely and quickly into a pregnant female's vagina and affixed her cervix.

It is a further objective of the invention to provide a device which is neither obtrusively large nor unduly delicate in use such that it does not pose a burden to the female patient/subject or suffer damage under normal conditions of use.

It is a yet further objective of the invention to provide a device which may be used with pregnant female subjects who may be human or non-human.

To these ends, a preferred embodiment of the invention includes a hollow housing having a cavity in which an electronic unit is disposed. The electronic unit comprises a tension sensor which is in electronic communication with a transmitter and further comprises a source of electric power. The housing is manufactured from a bio-compatible material and is saucer-shaped. The top surface of the housing has a central hole through which a spindle is inserted. At one end, the spindle is capped with a tension knob and at the opposing end it is connected to the electronic unit. A plurality of sutures terminating at a first end in suture anchors are attached at a second end to the spindle within the cavity, are guided over suture guides and threaded through respective pores in the bottom surface of the housing.

In use, the device is inserted into the vagina of a female subject and is secured to the tissue of her cervix by the suture anchors. The tension knob is rotated to reel in the sutures and to remove slack therefrom. Dilatation of the cervix causes tension in the sutures exerted on the spindle. The tension sensor translates the tension exerted on the spindle into a trigger signal which is communicated to the transmitter. Thereafter and in response to the trigger signal, the transmitter emits a signal to an auxiliary electronic device such as a computer. During the first phase of labor, the tension sensor continuously or intermittently communicates the state of dilatation to the transmitter, which is communicated to the computer. The computer may compile the multiple communications from the transmitter for graphical presentation to a health caregiver. Moreover, by selecting unique transmitting frequencies for each device, data from several patients may be compiled by a single computer so that the health caregiver may review the state of dilatation in all of her patients in a rapid review.

BRIEF DESCRIPTION OF THE DRAWINGS

The present invention will be better understood with reference to the appended drawing sheets, wherein.

DETAILED DESCRIPTION

Figure 1:
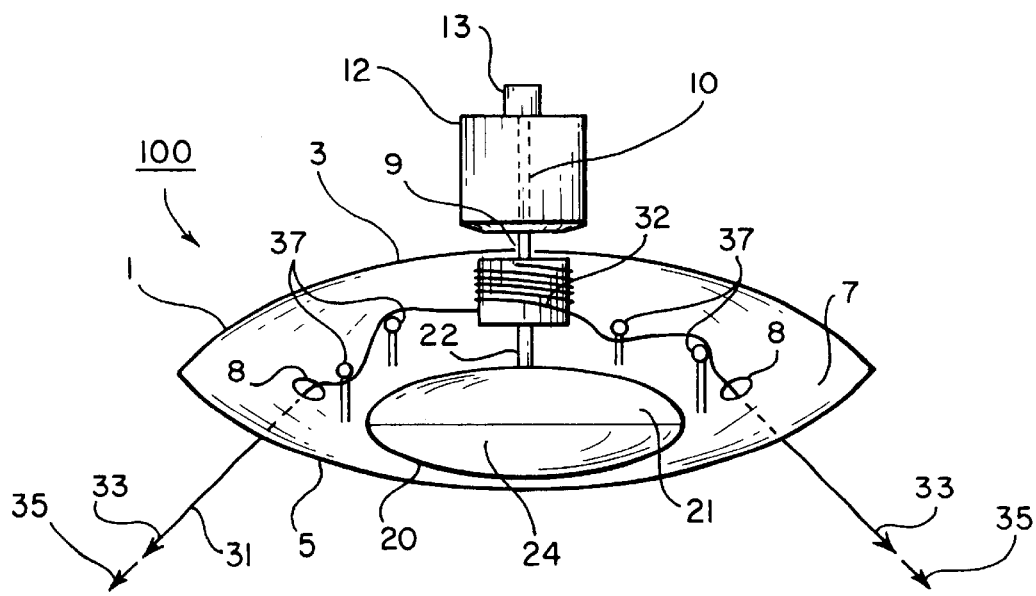
FIG. 1 is a side section detail of the labor monitoring device of the instant invention.
Figure 6:
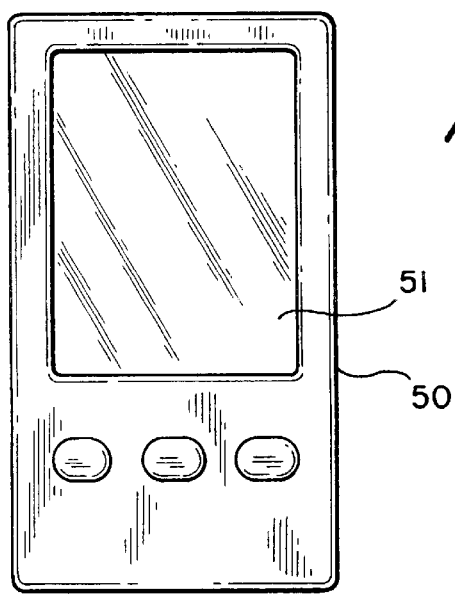
FIG. 6 is a side view of a secondary electronic device for use with the labor monitoring device of the present invention.
Figure 2:
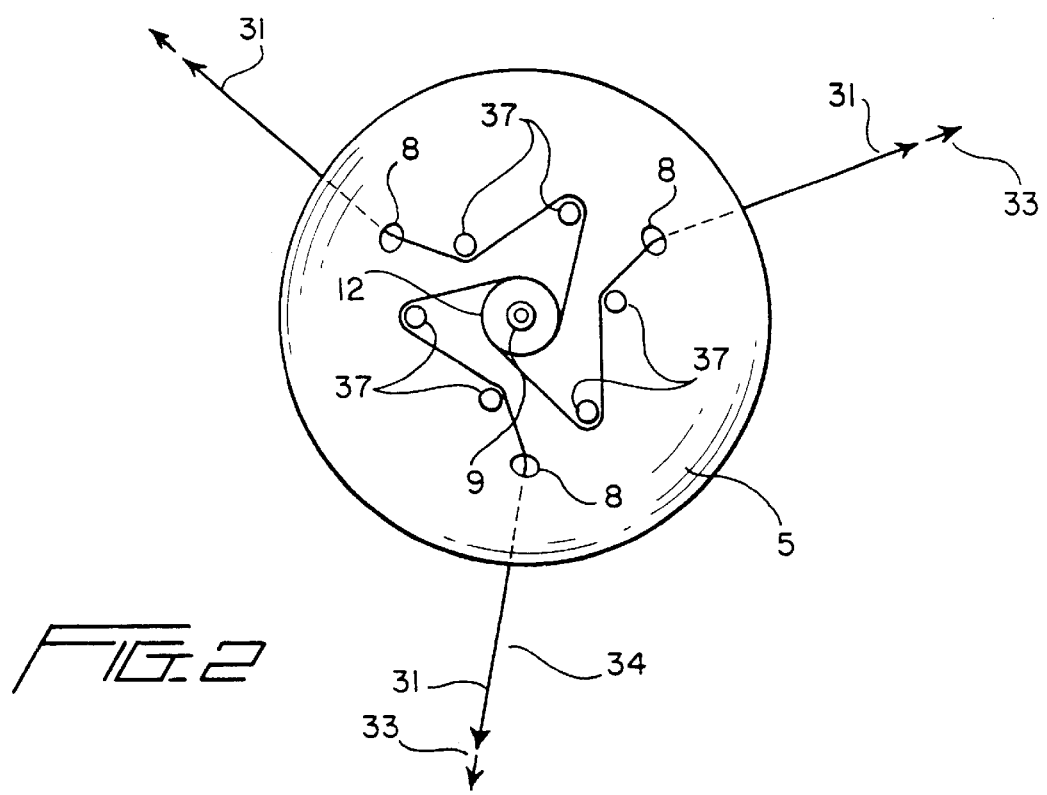
FIG. 2 is a bottom perspective view of the labor monitoring device of the instant invention.

Referring to the reference numerals of FIGS. 1 and 2, the labor monitoring device 100 of the instant invention is seen to comprise a saucer-shaped hollow housing 1 having a top surface 3, a bottom surface 5, a cavity 7, a central hole 9 within said top surface and a plurality of pores 8 radially distributed in said bottom surface. The housing is manufactured from a bio-compatible material such as PTFE, HDPE and the like. Within the cavity 7 an electronic unit 20 is housed which comprises a power source 21, a tension sensor 22 such as a transducer and a transmitter 24. The power source provides electrical energy to both the tension sensor and the transmitter which are in electric communication with each other.

A spindle 10 provided with a tension knob 12 penetrates the surface of the housing at the central hole 9 and is functionally joined to the electronic unit 20. A plurality of sutures 31 each having a first end 32 and a second end 33 separated by a length of thread 34 are also housed within the housing 1. Each suture is fixedly joined to the spindle 10 by said respective first end 32 and is guided by a respective suture guide 33 until at some length of thread 34, the second end of each suture is threaded through a respective one of said plurality of pores 8. The second ends 33 of each of the sutures is provided with a suture anchor 35 which may be affixed to the cervix 90 of a pregnant female subject.

When a female patient is admitted to a hospital or birthing center during the first phase of labor, the labor monitoring device of the instant invention 100 is affixed to her cervix by the suture anchors in a relatively simple surgical treatment. The length of thread 34 is gathered up on the spindle 10 by manually winding the tension knob 12 until no slack is left in the sutures. A set button 13 of the tension knob may be depressed to maintain the desired position of the wound spindle.

Figure 3:
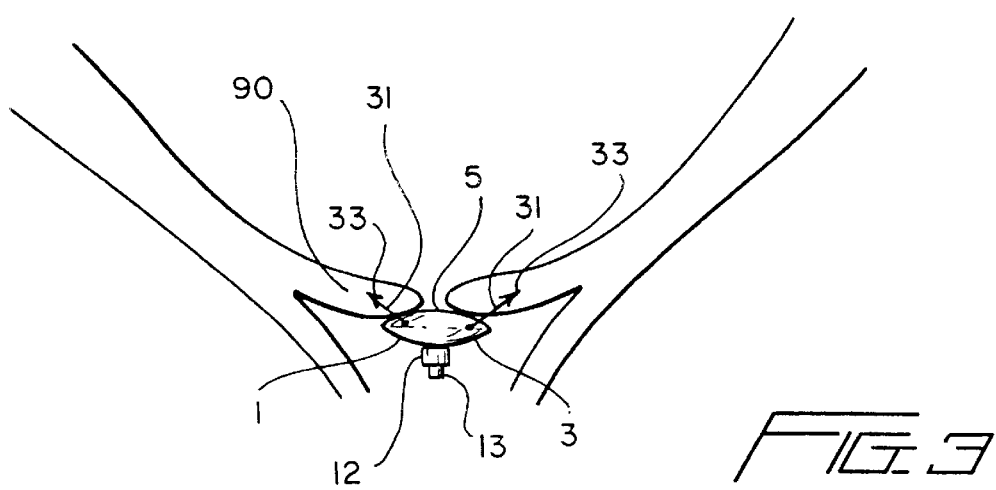
FIG. 3 is a side sectional detail of the female uterus and cervix showing the placement of the labor monitoring device of the instant invention when affixed thereto.

As shown in FIG. 3, the labor alerting device is affixed in a female subject's cervix 90 in such manner that that the bottom surface 5 is in contact with the cervix, whereas the top surface, tension knob 12 and set button 13 are accessible by medical personnel through the vagina of the female.

Figure 4:
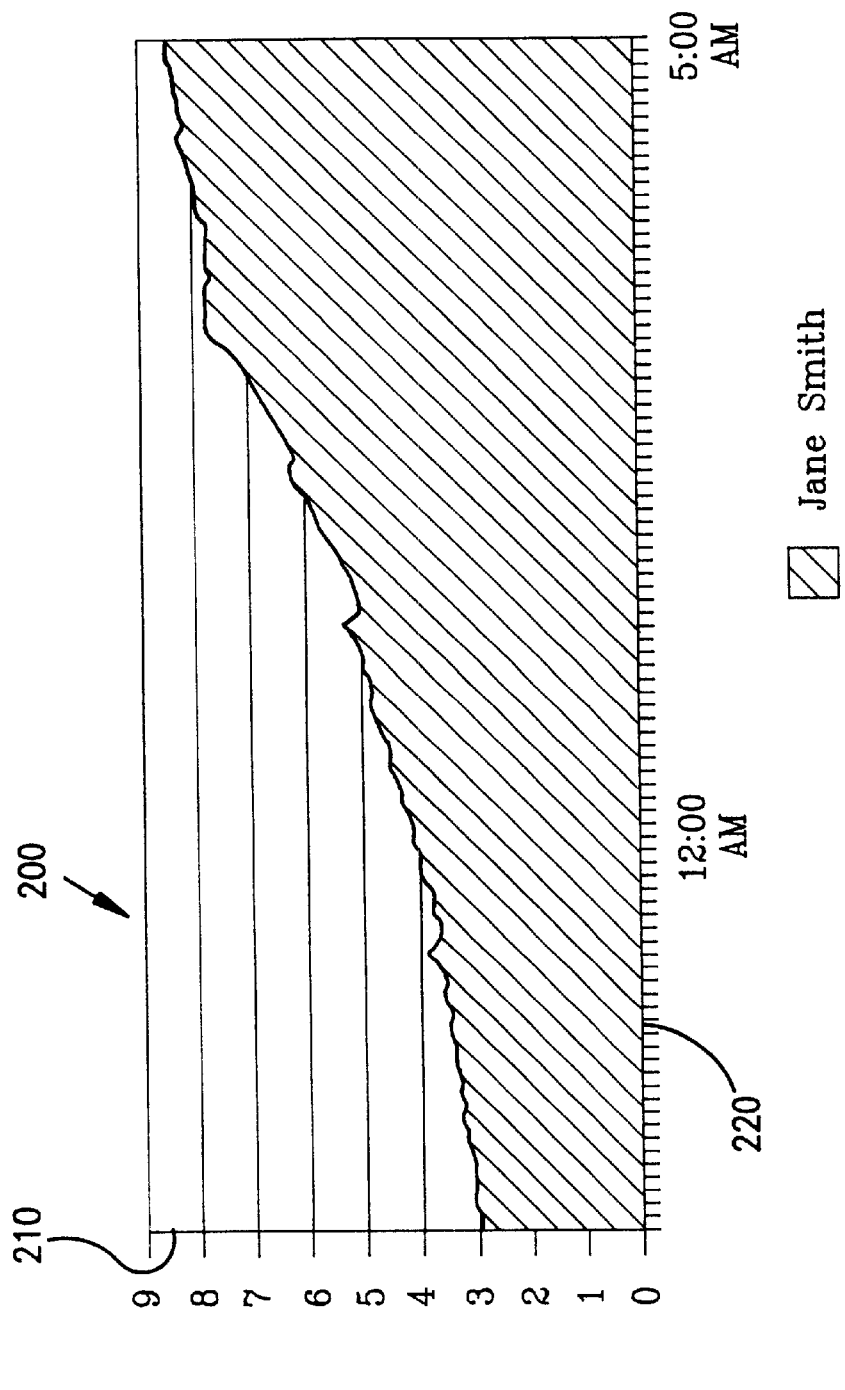
FIG. 4 is a graphical representation showing cervical dilation plotted over time for a single patient.

The dilatation of the cervix 90 exerts tension on the sutures 31, thereby effecting a counter-rotation of the spindle 10. The tension sensor 22 of the electronic unit 20 translates the tension exerted on the spindle to a signal communicated to the transmitter 24. The transmitter 24 emits an electronic signal to a second electronic device 50 having an interface 51 such as a computer or monitor, notifying a person viewing the interface of the amount by which the cervix 90 of a female has dilated. During the first phase of labor, the tension sensor continuously or intermittently communicates the state of dilatation to the transmitter, which is communicated to the computer. The computer may compile the multiple communications from the transmitter for graphical presentation to a health caregiver. For example, FIG. 4 shows a sample graph 200 plotting dilation in centimeters (y axis) 210 over time (x axis) 220, presenting a complete dilation record for a sample patient "Jane Smith." The constant monitoring via the labor monitoring device has obviated the need for continuous manual measuring by the health caregiver during the time period shown.

Figure 5:
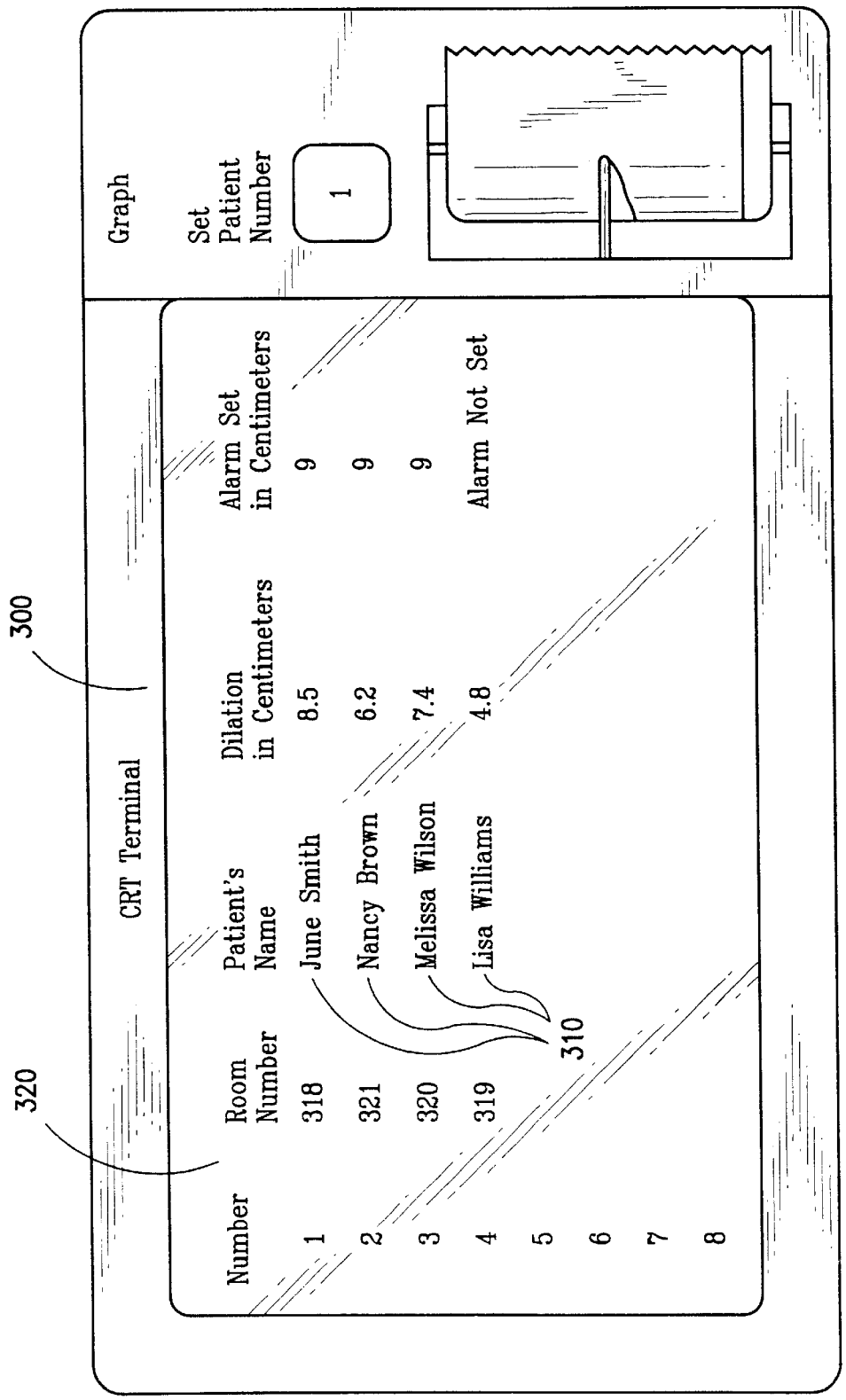
FIG. 5 is a graphical representation showing cervical dilation data from multiple patients compiled on a single computer screen.

The transmitting frequency of the labor monitoring device 100 may be individualized such that each female patient may be correlated with a unique frequency making individual tracking possible. As shown in FIG. 5, a computer 300 may be slaved to multiple labor monitoring devices each associated with a respective patient 310 so that the health caregiver may quickly view the states of multiple patients from a single display 320.

The components of the labor monitoring device 100 are relatively inexpensive, thus they may be discarded after use preventing the spread of communicable diseases.

Exemplary modifications, enumerated herein, have been given to illuminate rather than to limit the scope of the invention. While particular embodiments of the invention have been described, it will be understood, of course, that the invention is not limited thereto, and that many obvious modifications and variations can be made, and that such modifications and variations are intended to fall within the scope of the appended claims.

What is claimed is:

1. A labor monitoring device comprising:
   an auxiliary electronic device;
   a housing, said housing being saucer shaped and having a cavity, top surface, a bottom surface, a central hole within said top surface and a plurality of pores radially distributed through said bottom surface;
   a spindle member, said spindle member being positioned within said central hole such that it penetrates said top surface to said cavity;
   a tension knob affixed to said spindle member at said top surface of said housing;
   a plurality of suture guides within said cavity;
   a plurality of sutures, each of said sutures have a first end, a second end and a length, each of said sutures being affixed to said spindle member at respective first ends, each of said lengths being guided by a respective one of said suture guides and being threaded through a respective one of said plurality of pores and each of said sutures terminating in a suture anchor at said second ends;
   an electric power source;
   an electronic tension sensor, said tension sensor being in electrical communication with said electric power source and being functionally related to said spindle member, whereby said tension sensor is responsive to tension exerted by said plurality of sutures on said spindle member;
   a transmitter, said transmitter being in electrical communication with said electric power source and being in electronic communication with said electronic tension sensor, whereby an electronic communication generated by said tension sensor and electronically communicated thereby to said transmitter causes said transmitter to emit a signal to said auxiliary electronic device, said auxiliary electronic device having an interface and being capable of displaying tension conditions sensed by said tension sensor to a health caregiver.

2. The labor monitoring device of claim 1 wherein said auxiliary electronic device is a computer.

3. The labor monitoring device of claim 1 wherein said auxiliary electronic device is a monitor.

4. The labor monitoring device of claim 1 wherein said tension sensor and said transmitter are in continuous electronic communication with said auxiliary electronic device, such that said auxiliary electronic device provides continuous monitoring of tension exerted by said plurality of sutures upon said spindle member.

5. The labor alerting device of claim 1 wherein said labor alerting device is manufactured from a bio-compatible material.

6. The labor alerting device of claim 5 wherein said labor alerting device is suitable for implantation on the cervix of a female mammal.

7. The labor alerting device of claim 6 wherein said female mammal is a human female.

8. A method for using the labor monitoring device of claim 1 comprising the steps of:
   affixing said plurality of suture anchors to the cervix of a female mammal;
   tightening said plurality of sutures by rotating said spindle member to reduce slack in said plurality of sutures until a desired tension in said sutures obtains;
   whereby dilation of said cervix is converted to a tension in said sutures, said tension being translatable by said tension sensor into data communicatable by said tension sensor to said transmitter, said transmitter emitting a signal to said auxiliary electronic device, whereby said auxiliary electronic device communicates dilation information on said interface to a health caregiver.

\* \* \* \* \*